(12) United States Patent
Franciskovich et al.

(10) Patent No.: US 8,043,845 B2
(45) Date of Patent: Oct. 25, 2011

(54) STERILIZATION INDICATOR

(75) Inventors: Phillip P. Franciskovich, Concord, OH (US); Tricia A. Cregger, Fairlawn, OH (US); Mark J. Duda, Twinsburg, OH (US)

(73) Assignee: American Sterilizer Company, Mentor, OH (US)

(*) Notice: Subject to any disclaimer, the term of this patent is extended or adjusted under 35 U.S.C. 154(b) by 30 days.

(21) Appl. No.: 11/533,487

(22) Filed: Sep. 20, 2006

(65) Prior Publication Data
US 2008/0070272 A1 Mar. 20, 2008

(51) Int. Cl.
*C12M 3/00* (2006.01)

(52) U.S. Cl. .................... 435/287.4; 435/31

(58) Field of Classification Search ........... 435/287.4, 435/31, 810, 832; 422/58, 61
See application file for complete search history.

(56) References Cited

U.S. PATENT DOCUMENTS

| | | | |
|---|---|---|---|
| 2,854,384 A | 9/1958 | Beakley et al. | 195/54 |
| 3,239,429 A | 3/1966 | Menolasino et al. | 195/54 |
| 3,346,464 A | 10/1967 | Ernst | 195/54 |
| 3,440,144 A | 4/1969 | Andersen | 195/103.5 |
| 3,551,295 A | 12/1970 | Dyer | 195/103.5 |
| 3,585,112 A | 6/1971 | Ernst | 195/103.5 |
| 3,661,717 A | 5/1972 | Nelson | 195/103.5 |
| 3,752,743 A | 8/1973 | Henshilwood | 195/127 |
| 3,796,635 A | 3/1974 | Delente | 195/65 |
| 3,846,242 A | 11/1974 | Ernst | 195/103.5 |
| 4,011,139 A | 3/1977 | Horwath et al. | 195/65 |
| 4,162,942 A | 7/1979 | Gunther | 435/17 |
| 4,284,719 A | 8/1981 | Agerhem et al. | 435/18 |
| 4,291,122 A | 9/1981 | Orelski | 435/31 |
| 4,304,869 A | 12/1981 | Dyke | 435/296 |
| 4,348,209 A | 9/1982 | Murtaugh et al. | 23/232 |
| 4,416,984 A | 11/1983 | Wheeler, Jr. | 435/31 |
| 4,448,548 A | 5/1984 | Foley | 374/160 |
| 4,461,837 A | 7/1984 | Karle et al. | 435/296 |

(Continued)

FOREIGN PATENT DOCUMENTS

EP 0000063 A1 12/1978

(Continued)

OTHER PUBLICATIONS

Geoffrey Zubay; Biochemistry, Third Edition; Wm. C. Brown Publishers, 1993; pp. 867 and 868.

(Continued)

*Primary Examiner* — Ralph Gitomer
(74) *Attorney, Agent, or Firm* — Renner, Otto, Boisselle & Sklar, LLP

(57) ABSTRACT

The disclosed technology relates to a sterilization indicator and a process to concentrate signal generated by constraining it to a minimal surface, in a minimal volume and minimal pH and growth buffering or mediating influences. The sterilization indicator may comprise a carrier 12, the carrier having a first surface 14 and a second surface 16; a support 20, the support having a first section 22 and a second section 24, the carrier 12 overlying the first section 12 of the support 20, the second surface 16 of the carrier being adhered to the first section 22 of the support 20; and a biological indicator 30 supported by the carrier 12. The second section 24 of the support 20 may be of sufficient dimension to permit handling the sterilization indicator 10 without contacting the biological indicator 30. A process for making the sterilization indicator is disclosed. Processes for using the sterilization indicator are disclosed.

32 Claims, 3 Drawing Sheets

U.S. PATENT DOCUMENTS

| | | | |
|---|---|---|---|
| 4,528,268 A | 7/1985 | Andersen et al. | 435/31 |
| 4,579,823 A * | 4/1986 | Ryder | 435/287.4 |
| 4,580,682 A | 4/1986 | Gorski et al. | 206/569 |
| 4,591,554 A | 5/1986 | Koumura et al. | 435/18 |
| 4,596,773 A | 6/1986 | Wheeler, Jr. | 435/31 |
| 4,603,108 A | 7/1986 | Bascomb | 435/34 |
| 4,717,661 A | 1/1988 | McCormick et al. | |
| 4,743,537 A | 5/1988 | McCormick et al. | |
| 4,883,641 A | 11/1989 | Wicks et al. | 422/50 |
| 5,073,488 A | 12/1991 | Matner et al. | 435/31 |
| 5,079,144 A | 1/1992 | Carr et al. | 435/32 |
| 5,223,401 A | 6/1993 | Foltz et al. | 435/18 |
| 5,252,484 A | 10/1993 | Matner et al. | 435/288 |
| 5,366,872 A | 11/1994 | Hird et al. | 435/31 |
| 5,405,580 A | 4/1995 | Palmer | 422/28 |
| 5,418,167 A | 5/1995 | Matner et al. | 435/288 |
| 5,486,459 A | 1/1996 | Burnham et al. | 435/31 |
| 5,739,004 A | 4/1998 | Woodson | 435/31 |
| 5,770,393 A | 6/1998 | Dalmasso et al. | 435/31 |
| 5,830,683 A | 11/1998 | Hendricks et al. | 435/31 |
| 5,870,885 A | 2/1999 | Biddle et al. | 53/436 |
| 5,989,852 A | 11/1999 | Hendricks et al. | 435/31 |
| 6,025,189 A | 2/2000 | Bolea et al. | 435/287.4 |
| 6,063,591 A | 5/2000 | Bolea | 435/31 |
| 6,355,448 B1 | 3/2002 | Foltz et al. | 435/31 |
| 6,566,090 B2 | 5/2003 | Witcher et al. | 435/31 |
| 6,623,955 B2 | 9/2003 | Matner et al. | 435/287.4 |
| 6,924,139 B2 | 8/2005 | Eveland et al. | 435/287.4 |
| 6,942,989 B2 | 9/2005 | Felkner et al. | 435/31 |
| 7,326,562 B2 * | 2/2008 | Felkner et al. | 435/287.4 |
| 7,416,883 B2 * | 8/2008 | Cregger et al. | 435/287.4 |
| 2003/0064507 A1 | 4/2003 | Gallagher et al. | 435/287.2 |
| 2003/0157588 A1 | 8/2003 | Matner et al. | |
| 2008/0070231 A1 * | 3/2008 | Franciskovich et al. | 435/5 |
| 2009/0047176 A1 * | 2/2009 | Cregger et al. | 422/28 |
| 2009/0117603 A1 * | 5/2009 | Franciskovich et al. | 435/19 |
| 2010/0081165 A1 * | 4/2010 | Pasmore et al. | 435/31 |

FOREIGN PATENT DOCUMENTS

| | | |
|---|---|---|
| GB | 1547747 A | 6/1979 |
| GB | 2128204 A | 4/1984 |
| GB | 2186974 A | 8/1987 |
| WO | 8605206 A1 | 9/1986 |

OTHER PUBLICATIONS

Haruhisa Hirata et al.; Journal of Bacteriology, "Structure of a β-Galactosidase Gene of *Bacillus stearothermophilus*"; Jun. 1986; pp. 722-727.

Haruhisa Hirata et al.; Applied and Environmental Microbiology, "High Production of Thermostable β-Galactosidase of *Bacillus stearothermophilus* in *Baccilus subtilis*"; Jun. 1985; pp. 1547-1549.

Tohru Shimizu et al.; Proceedings of the National Academy or Sciences of the United States of America, vol. 99, No. 2, "Complete Genome Sequence of *Clostridium perfringens*, an Anaerobic Flesheater"; Jan. 2002; pp. 996-1001.

J. Hahn et al.; Molecular Microbiology, "Regulatory Inputs for the Synthesis of ComK, the Competence Transcription Factor of *Bacillus subtilis*"; 1996; pp. 763-775.

N.E. Welker et al.; "Induction of α-Amylase of *Bacillus stearothermophilus* by Maltodextrins"; J. Bacteriol, vol. 86, Apr. 1963; pp. 687-691.

http://textbookofbacteriology.net/regulation.html; Kenneth Todar University of Wisconsin-Madison Department of Bacteriology; "Regulation and Control of Metabolic Activity"; 2004; pp. 1-11.

http://textbookofbacteriology.net/nutgro.html; Kenneth Todar University of Wisconsin-Madison Department of Bacteriology; "Nutrition and Growth of Bacteria"; 2004; pp. 1-17.

U.S. Appl. No. 11/533,522, filed Sep. 20, 2006.

International Search Report and Written Opinion, Application No. PCT/US07/78843, mailed Aug. 11, 2008.

* cited by examiner

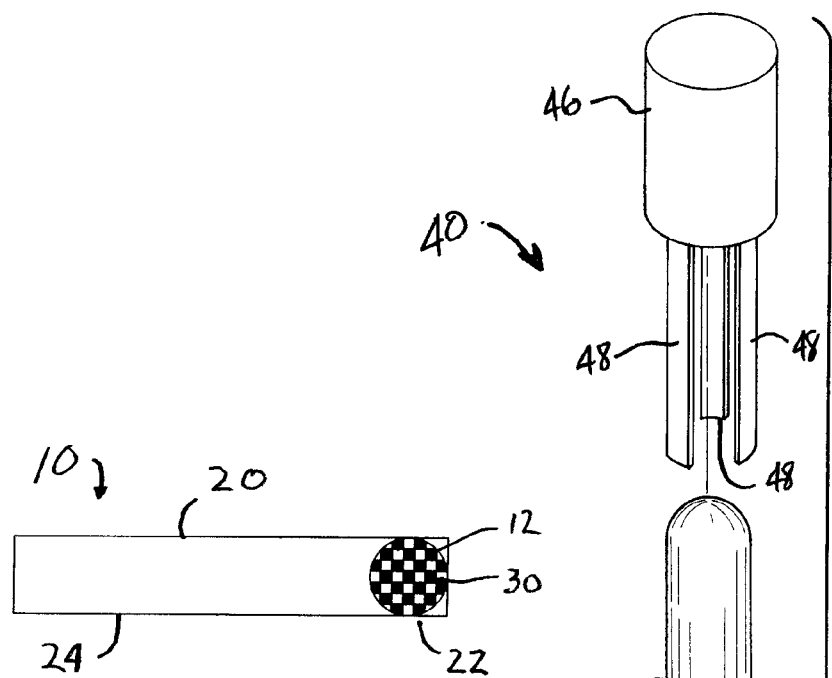
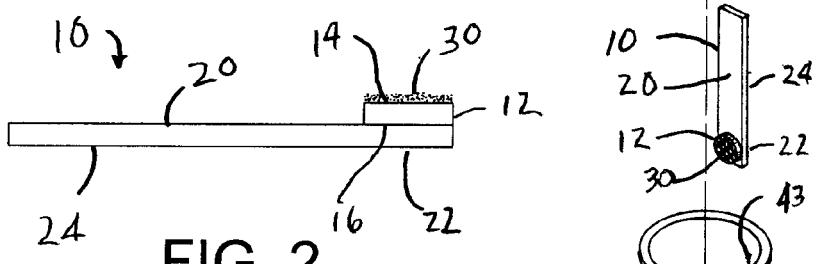
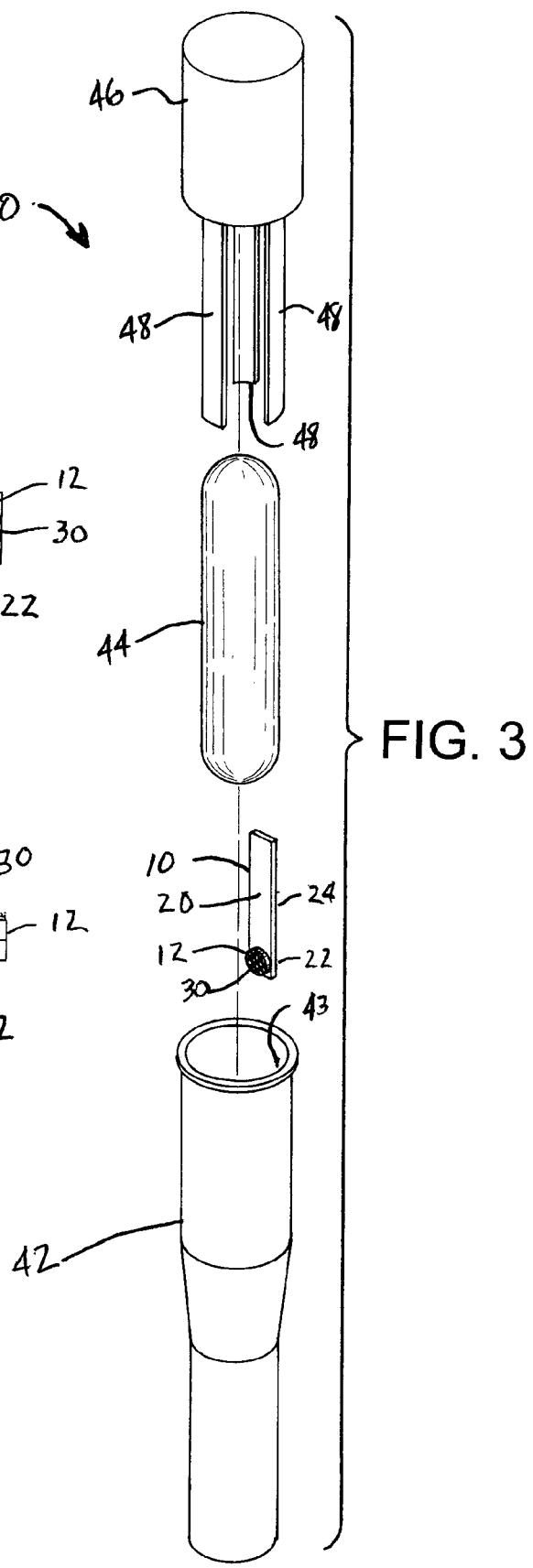
FIG. 1
FIG. 2
FIG. 3

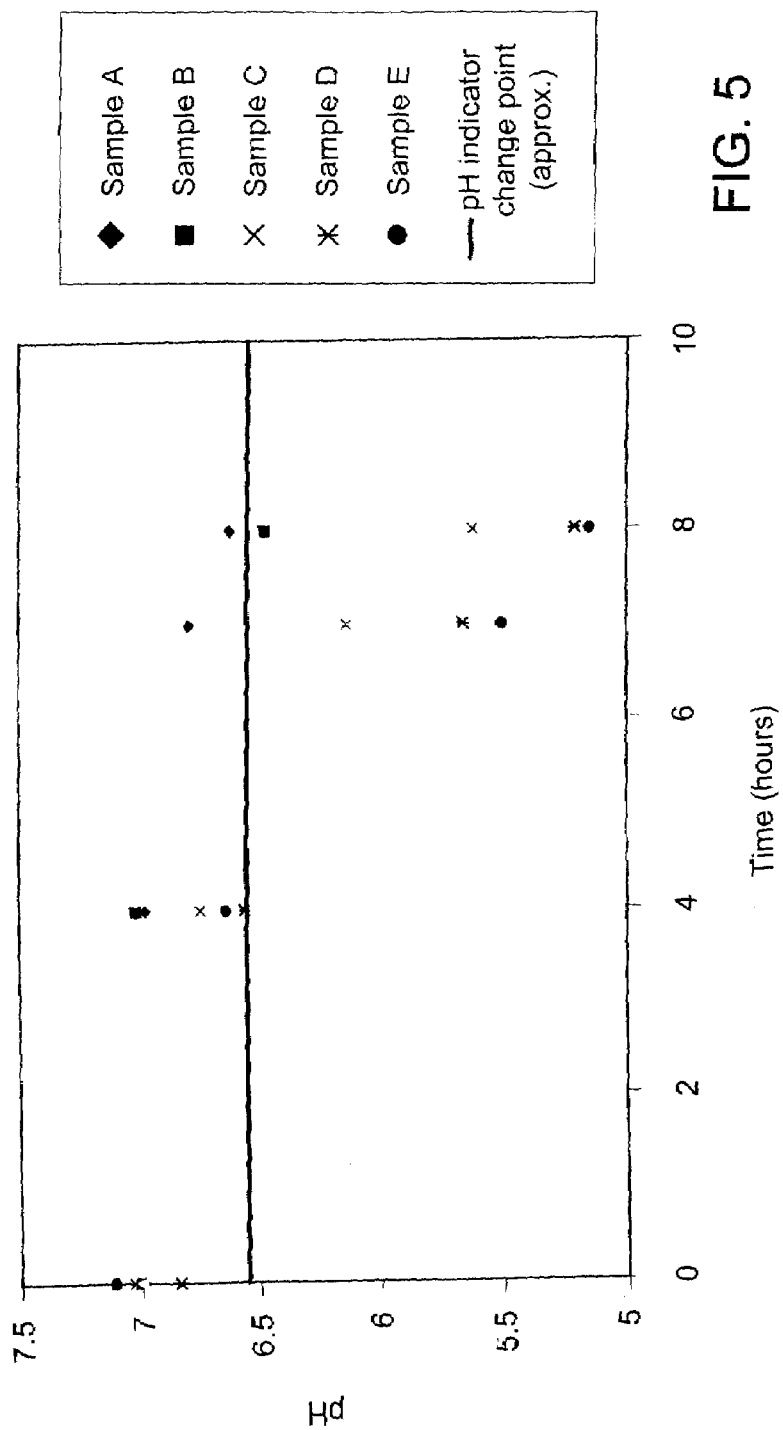

STERILIZATION INDICATOR

TECHNICAL FIELD

The disclosed technology relates to a sterilization indicator, and to a process for making the sterilization indicator. The disclosed technology relates to a sterilization process using the sterilization indicator to determine the effectiveness of sterilization.

BACKGROUND

Primarily in the health care industry, but also in many other commercial and industrial applications, it is often necessary to monitor the effectiveness of the processes used to sterilize equipment such as medical and non-medical devices, instruments and other articles and materials. It is often standard practice in these sterilization processes to include a sterilization indicator in the batch of articles to be sterilized. This allows a direct approach to assay the lethality of the sterilization process.

Conventional sterilization indicators typically contain a biological indicator. The biological indicator may comprise one or more test organisms which are designed to be more resistant to the sterilization process than the organisms to be destroyed by the sterilization. These test organisms are usually bacterial spores. Conventional sterilization indicators may be available in two forms.

The first of these forms involves the use of a substrate wherein bacterial spores are directly applied or inoculated on the substrate. The substrate may be fully covered with the spores. Any physical handling by the user may result in spores being lost from the substrate, transferred to the user, or potentially contaminating or being contaminated by the surrounding area. It has been proposed to provide special clips to allow the user to handle the substrate. However, these clips often hinder the sterilization process and may result in a faulty test result. Also, minimum size constraints for these substrates typically lead to the requirement for relatively large volumes of incubation medium, for example, from about 5 to about 10 milliliters (ml), and relatively long incubation periods, for example, from about 2 to about 7 days.

The second of these forms involves a self-contained sterilization indicator. These sterilization indicators typically contain the bacterial spores and the incubation medium in a single container, but in separate compartments. The spores are subjected to the sterilization process. Following sterilization, the container is activated so that any surviving spores may come into contact with the incubation medium to determine the effectiveness of the sterilization. These sterilization indicators may be useful in gaseous sterilization processes, but are typically not suitable for liquid sterilization processes.

A major drawback with each of these sterilization indicators relates to the time delay in obtaining results for the sterilization test. These sterilization indicators normally require that the bacterial spores be cultured for at least two and often up to about seven days to assure adequate detection of any surviving spores. During this time, the articles that went through the sterilization process and are under evaluation should not be used until the results of the spore viability test have been determined. However, many health care facilities have limited resources and must reuse their "sterilized" instruments within 24-48 hours and often immediately. In such settings, the two to seven day holding period for sterility verification may be impractical, costly and inefficient.

Thus, a problem that has been presented by the art is to provide a sterilization indicator that minimizes or eliminates the handling of the biological indicator and accurately detects the effectiveness of a sterilization process within a relatively short period of time. It would be advantageous if this sterilization indicator could be adaptable to liquid sterilization processes as well as gaseous sterilization processes. The disclosed technology, in at least one embodiment, may provide a solution to this problem.

SUMMARY

The disclosed technology may relate to a sterilization indicator, comprising: a carrier, the carrier having a first surface and a second surface; a support, the support having a first section and a second section, the carrier overlying the first section of the support, the second surface of the carrier being adhered to the first section of the support; and a biological indicator supported by the carrier, the second section of the support being of sufficient dimension to permit handling the sterilization indicator without contacting the biological indicator.

The disclosed technology may relate to a sterilization indicator kit, comprising: a first compartment, containing the above-indicated sterilization indicator, the first compartment being adapted to permit the sterilization indicator to be brought into contact with a sterilization medium during sterilization; and a second compartment containing an incubation medium, the second compartment being adapted to maintain the incubation medium separate from the sterilization indicator during sterilization, and the second compartment being adapted to permit the incubation medium to contact the sterilization indicator after the sterilization indicator has been exposed to the sterilization medium.

The disclosed technology may relate to a process for making the above-indicated sterilization indicator, comprising: applying the biological indicator to the carrier; and adhering the carrier to the support.

The disclosed technology may relate to a sterilization process, comprising: exposing an article to be sterilized and the above-indicated sterilization indicator to a sterilization medium.

The disclosed technology may relate to a process for determining the effectiveness of sterilization, comprising: exposing an article to be sterilized and the above-indicated sterilization indicator to a sterilization medium, the biological indicator comprising at least one test organism; and contacting the carrier with an incubation medium after sterilization to determine whether the sterilization is effective.

The disclosed technology may relate to a process for determining the effectiveness of sterilization, comprising: exposing at least one article to be sterilized and the above-indicated sterilization indicator to a sterilization medium, the biological indicator comprising at least one enzyme; and contacting the carrier with at least one enzyme substrate to determine whether the sterilization is effective.

BRIEF DESCRIPTION OF THE DRAWINGS

In the annexed drawings, like parts and features have like references.

FIG. 1 is a plan view of a schematic illustration of one embodiment of the disclosed sterilization indicator.

FIG. 2 is a schematic illustration of a side elevation of the sterilization indicator depicted in FIG. 1.

FIG. 3 is an exploded schematic illustration of an apparatus for determining the effectiveness of sterilization, the apparatus containing two compartments, the foregoing sterilization indicator being positioned in one compartment and an incubation medium being positioned in the other compartment.

FIG. 5 is a plot of pH as a function of growth of spores of *Geobacillus stearothermophilus* exposed to incubation media of different volumes and buffering capacities as disclosed in Example 2.

DETAILED DESCRIPTION

Figure 4:
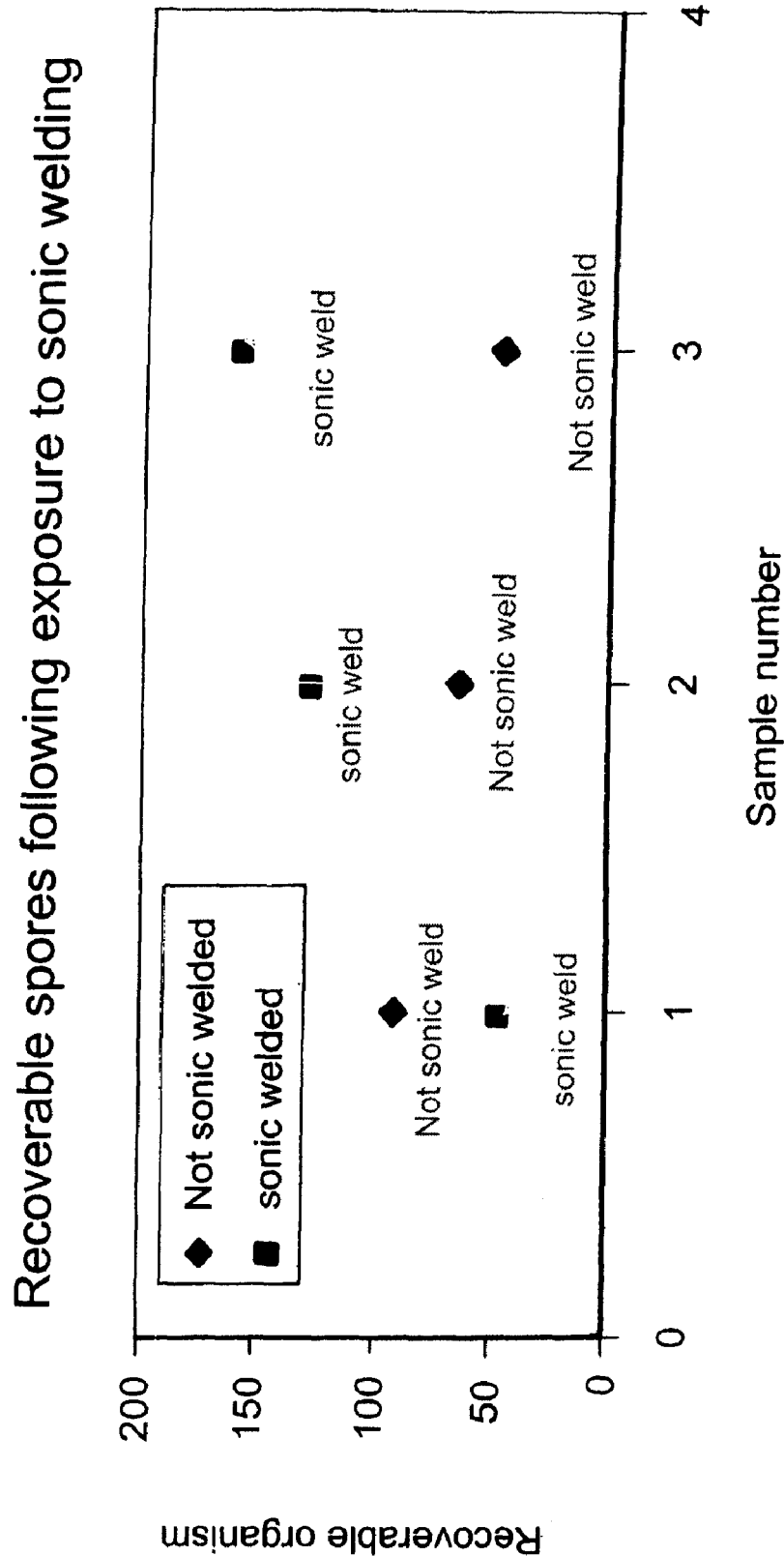
FIG. 4 is a plot of recoverable spores for samples of the disclosed sterilization indicator in Example 1, the plot indicating no significant difference in the number of viable spores following sonication as compared to prior to sonication.

The term "sterilization" may refer to rendering a substance incapable of reproduction, metabolism and/or growth. While this is often taken to mean total absence of living organisms, the term may be used herein to refer to a substance free from living organisms to a degree previously agreed to be acceptable. Unless otherwise indicated, the term sterilization may be used herein to also refer to methods and procedures less rigorous than sterilization, for example, disinfection, sanitization, and the like. The sterilization indicator and the processes and apparatus described herein may be used in health care fields, scientific fields, and the like. These may be used in commercial and industrial applications where sterilization, disinfection, sanitization, and the like, may be desired, for example, food processing, pharmaceutical manufacturing, and the like.

The sterilization process for which the disclosed sterilization indicator may be used may be any sterilization process. These may include sterilization processes wherein the sterilization medium or sterilant may be steam, dry heat, radiation, as well as one or more gaseous sterilants, one or more liquid sterilants, and the like. The radiation may comprise electron beam or any electromagnetic spectra including ionizing radiation, pulsed white or ultraviolet light, microwave, and the like. The radiation may comprise gamma or beta radiation. The gaseous sterilants may comprise ethylene oxide, gaseous hydrogen peroxide, and the like. The liquid sterilants may comprise formalin (formaldehyde gas dissolved in water and optionally containing methanol to inhibit the formation of toxic substances), glutaraldehyde, peracetic acid, liquid hydrogen peroxide, and the like.

The sterilization indicator may be used to examine the lethality of sterilants against any microorganism with less resistance to the sterilization process than the biological indicator used with the sterilization indicator. These microorganisms may include bacteria such as *Escherichia coli*, *Legionella* sp., *Campylobacter* sp., and other enteric bacteria, as well as *Staphylococcus* and *Streptococcus* species and other human pathogenic microorganisms such as *Cryptosporidium*.

The sterilization indicator may be described with reference to FIGS. 1 and 2. Referring to these figures, sterilization indicator 10 may comprise carrier 12, the carrier 12 having a first surface 14 and a second surface 16; support 20, the support 20 having a first section 22 and a second section 24, the carrier 12 overlying the first section 22 of the support 20, the second surface 16 of the carrier 12 being adhered to the first section 22 of the support 20; and biological indicator 30 supported by the carrier 12. The biological indicator 30 may be supported by or adhered to the first surface 14 of the carrier 12. The second section 24 of the support 20 may be of sufficient dimension to permit handling the sterilization indicator 10 without contacting the biological indicator 30. That is, the second section 24 may be of sufficient dimension to function as a handle thereby permitting facilitated aseptic handling of the sterilization indicator 10.

The carrier 12 may be in the form of a relatively flat substrate which is depicted in the drawings as being in the form of a circle. However, it is to be understood that the carrier 12 may have any desired shape or form, for example, square, rectangle, oval, and the like. The carrier 12 may have a prismatic cross-section. The carrier 12 may have a thickness that is relatively small, for example, from about 0.001 to about 3 mm, and in one embodiment from about 0.01 to about 2 mm, and in one embodiment from about 0.05 to about 1.5 mm, and in one embodiment from about 0.1 to about 1 mm. The area of the first surface 14 of the carrier 12, which provides support for the biological indicator 30, may be relatively small, for example, the area may be in the range from about 1 to about 80 $mm^2$, and in one embodiment from about 2 to about 70 $mm^2$, and in one embodiment from about 3 to about 60 $mm^2$, and in one embodiment from about 5 to about 50 $mm^2$. An advantage of such a small area is that the size of the biological indicator 30 may be relatively small, and consequently the amount of incubation medium needed to incubate the biological indicator may be relatively small and the time requirement for incubation may be relatively short.

The carrier 12 may comprise a porous material or a non-porous material. The carrier may comprise a solid carrier. The carrier may comprise any material that does not dissolve or deteriorate during the sterilization or incubation processes. The carrier 12 may comprise paper, metal, glass, ceramics, plastic, membranes, or a combination of two or more thereof. The metal may comprise aluminum or steel. The plastic may comprise a polyolefin, polystyrene, polycarbonate, polymethacrylate, polyacrylamide, polyimide, polyester, and the like. The carrier 12 may comprise a film. The carrier may be in the form of a spun or unwoven felt. The carrier may comprise a mat of compressed fibers. The carrier may comprise a porous material made of sintered glass, glass fibers, ceramic, synthetic polymer, or a combination of two or more thereof. The carrier may comprise filter paper or absorbent paper. The carrier may comprise a cellulose pad.

The support 20 may comprise any material that does not dissolve or disintegrate during the sterilization or incubation processes. The support may comprise metal, glass, ceramic, plastic, or a combination thereof. The support may comprise aluminum or stainless steel. The support may comprise polystyrene, polyolefin (e.g., polypropylene, polyethylene), and the like. The support 20 may be flexible or rigid. The support 20 may be foldable. The support 20 depicted in the drawings is rectangular in shape, however, it is to be understood that the support may have any desired shape or form, for example, square, circle, oval, and the like. The length of the support 20 may be in the range from about 0.2 to about 12 cm, and in one embodiment from about 0.2 to about 10 cm, and in one embodiment from about 0.5 to about 7 cm, and in one embodiment from about 1 to about 5 cm, and in one embodiment from about 1.5 to about 3.5 cm. The width of the support 20 may be in the range from about 0.2 to about 2 cm, and in one embodiment from about 0.2 to about 1.5 cm, and in one embodiment from about 0.25 to about 1 cm. The thickness of the support 20 may be in the range from about 0.02 to about 3 mm, and in one embodiment from about 0.1 to about 2 mm. The length of the second section 24 may be in the range from about 0.2 to about 12 cm, and in one embodiment from about 0.3 to about 11 cm, and in one embodiment from about 0.5 to about 10 cm, and in one embodiment from about 1 to about 7 cm, and in one embodiment from about 1.5 to about 4.5 cm.

The support 20 may be in the form of a rectangular sheet or strip, the first section 22 of the support 20 comprising a minor part of the length of the carrier 20, the second section 24 of the support 20 comprising a major part of the length of the support 20. The ratio of the length of the second section 24 to the length of the first section 22 may be in the range from about 2:1 to about 12:1, and in one embodiment from about 4:1 to about 8:1, and in one embodiment from about 5.5:1 to about 6.5:1.

The carrier 12 may be attached to the support 20 using sonic welding, heat sealing, an adhesive, or lamination. The carrier 12 may be attached to the support 20 prior to or subsequent to applying the biological indicator 30 to the carrier 12. The carrier 12 may be attached to the support 20 subsequent to applying the biological indicator 30 to the support 12 using sonic welding or an adhesive. Sonic welding may involve frictional binding of the support to the carrier. The adhesive may be any adhesive that is compatible with the carrier 12 and the support 20, and does not dissolve or deteriorate during the sterilization or incubation processes. The adhesive should not be lethal or inhibitory to the organisms of interest. The adhesive may be a pressure sensitive adhesive.

The sterilization indicator 10 may be used in any process wherein the biological indicator 30 is exposed to a sterilization medium during a sterilization process and then to an incubation medium to determine whether the sterilization process was effective. The sterilization indicator 10 may be used with any sterilization process, for example, sterilization processes employing gaseous or liquid sterilants. The sterilization indicator 10 along with the articles to be sterilized may be exposed to a sterilization medium during a sterilization process. Upon completion of the sterilization process, the sterilization indicator 10 may be placed in a vial containing an incubation medium. The biological indicator 30 may then be incubated for a desired period of time and then examined to determine whether the sterilization process was effective.

The sterilization indicator 10 may be used in a self-contained sterilization indicator kit comprising a container with two separate compartments. One of the compartments may contain the sterilization indicator 10. The other compartment may contain an incubation medium. In use, the kit and the articles to be sterilized may be exposed to the sterilization medium. Then following sterilization, the kit may be activated so that the biological indicator 30 comes into contact with the incubation medium sufficiently to determine whether the sterilization process was effective. These kits may be used with any sterilization process wherein the biological indicator may be exposed to the sterilization medium, for example, sterilization processes employing gaseous sterilants.

The self-contained sterilization indicator kit may be in the form depicted in FIG. 3. Referring to FIG. 3, the kit 40 comprises tapered tube 42, inner compartment 44, and closure cap 46. The closure cap 46 includes projections 48. An annular space 43 is formed between the inner surface of tapered tube 42 and the outer surface of the inner compartment 44, the annular space 43 forming another interior compartment. The sterilization indicator 10 is positioned in the annular space 43. The incubation medium is contained in the inner compartment 44. The tapered tube 42 and the closure cap 46 may be made from any material that is compatible with the conditions and chemistries used in the sterilization process. These materials may include polycarbonate, polyolefins, polyamide, polymethacrylates, polymethylpentenes, polyesters, and the like. The inner compartment 44 may be in the form of a glass or frangible glass ampoule. Further details on the construction of tapered tube 42, inner compartment 44 and closure cap 46 may be found in U.S. Pat. No. 4,304,869, which is incorporated herein by reference. During sterilization, the kit 40, along with the articles to be sterilized, is exposed to the sterilization medium. When sterilization has been completed, the closure cap 46 is pressed downwardly into the tapered tube 42. The projections 48 press against the inner compartment 44 and cause it to rupture. This allows the incubation medium to contact biological indicator 30. After incubation for a predetermined time, the sterilization indicator 10 may be removed and the extent of sterilization may be determined by detecting change in the biological indicator 30.

The biological indicator 30 may comprise one or more test organisms. Alternatively, the biological indicator 30 may comprise one or more enzymes. The one or more enzymes may be derived from and/or isolated from one or more test organisms. The biological indicator 30 may comprise one or more test organisms in combination with one or more enzymes.

The test organism may comprise any organism whose resistance to the intended sterilization process exceeds that of the other organisms that are to be destroyed by the sterilization process. The type of test organism used as the biological indicator 30 may be dependent upon a variety of factors exemplified by, but not limited to, the type of sterilization process being used. The test organism may be a microorganism. The strains that may be used may be those that are the most resistant to the process used for sterilization. The test microorganism may comprise bacteria. The bacterial microorganisms may be those which form endospores, i.e., bacterial spores. The test organism may comprise bacteria of the *Bacillus* or *Clostridia* genera. These may include *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans*, and the like. The bacteria may comprise fungi, mycobacteria, protozoa, vegetative bacteria, and the like. Examples of fungi that may be used may include *Aspergillus niger, Candida albicans, Trichophyton mentagrophytes, Wangiella dermatitis*, and the like. Examples of mycobacteria that may be used may include *Mycobacterium chelonae, Mycobacterium gordonae, Mycobacterium smegmantis, Mycobacterium terrae*, and the like. Examples of protozoa that may be used may include *Giardia lamblia, Cryptosporidium parvum*, and the like. Examples of vegetative bacteria that may be used may include *Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Staphylococcus aureus, Staphylococcus epidermidis, Stenotrophomonas maltophilia*, and the like. Organisms such as *Geobacillus stearothermophilus, Bacillus atrophaeus, Bacillus subtilis, Bacillus coagulans, Clostridium sporogenes*, and the like, may be used for determining the efficacy of moist heat sterilization (autoclaving), with *Geobacillus stearothermophilus* being especially useful.

Microorganisms such as vegetative bacteria, vegetative cells and/or their constituent parts, which may be used as the test organism, may be deposited on the carrier 12 and survive drying and storage when deposited in the presence of one or more excipients. Excipients may be defined as a broad class of generally inert compounds that may be used to stabilize labile entities. A subclass of excipients that may be used includes the carbohydrates, for example, oligomeric and polymeric saccharides. An example of such a compound may be trehalose which is a disaccharide. High concentrations of trehalose in the tissues of certain organisms may allow the organisms to survive in a state of water deficiency. Trehalose may be used to revive functional cellular components after dehydration. Trehalose may provide stability to membranes and other macromolecular structures essential to the viability of a cell under extreme environmental conditions (e.g., freeze drying). Other stabilizing excipient compounds may include simple sugars (e.g. sucrose, glucose, maltose, and the like) and long chain polymers (e.g. dextrans, starch, agarose, cellulose, and the like). Other non-carbohydrate based excipients may include proteins, phosphonates, buffering agents, waxes, lipids, oils as well as other hydrocarbon based materials.

In addition to the simulative organisms selected on the basis of their acceptance as representing the most resistant organism (e.g. *Geobacillus stearothermophilus*), the biological indicator 30 may further comprise non self-replicating agents and/or sub-cellular components or products of cells. These may be used because of their clinical significance or because of their use as agents of bioterrorism. These organisms may comprise strains which may now have resistance to normal means of antibiotic treatment or chemical disinfection due to natural or man-made modifications. Examples of the former type may include VREs (Vancomycin Resistant enterococci), MSRAs (Methicillin Resistant *Staphylococcus aureus*), *Mycobacterium cheloni*, and the like. These may be used because the VREs and MRSAs have developed resistance to therapeutic countermeasures (e.g., antibiotic resistance) and *M. cheloni* has developed resistance to some modes of disinfection (e.g., glutaraldehyde resistance).

The biological indicator 30 may comprise one or more emerging organisms for which there may not yet be a simulative alternative. These may represent a special risk or challenge to therapeutic course of action or disinfection. Examples of these organisms may include prions. Prions are not living organisms, per se, but their function as disease causing agents may be related to their structure and this structure/function relationship may be employed to determine their relative infectivity. Other non-autonomous agents (e.g. viruses) as well as sub cellular elements and proteinaceous prions may be used as the biological indicator 30.

The carrier 12 may be inoculated with the test organism by preparing an aqueous suspension or dispersion comprising the test organism. The aqueous suspension or dispersion may comprise, for example, bacterial spores at a concentration ranging, for example, from about $10^5$ to about $10^{10}$ colony forming units (cfu) per milliliter, and in one embodiment from about $10^7$ to about $10^9$ cfu per milliliter. An aliquot of the suspension or dispersion may be placed on the carrier 12. For example, a suspension or dispersion of *B. subtilis* spores in water may be prepared to yield a desired number of spores per aliquot for inoculating the carrier 12. The spores may be allowed to dry on the carrier. An air flow may be used to dry the spores on the support, such as, for example, by placing the carrier in a laminar flow-hood to hasten the drying process. The method of drying the spores on the carrier may include allowing the spores to air dry by leaving them stand, placing the spores in a desiccator containing a desiccant such as calcium chloride, placing the spores in a laminar-flow hood, and the like. The number of colony forming units supported by the carrier 12 may be in the range from about $10^4$ to about $10^7$ cfu per square millimeter of support ($cfu/mm^2$), and in one embodiment in the range from about $10^5$ to about $10^6$ $cfu/mm^2$.

The sterilization indicator 10 may be used by subjecting it to the same sterilization medium and treatment as the articles for which sterile conditions may be sought. Heat may be applied and/or a gas, liquid, steam, or chemical and/or physical agent may pass into the area where the biological indicator 30 is located thereby exposing the biological indicator 30 to the same sterilization process or agent as the articles being sterilized. Following sterilization, an incubation medium may be brought into contact with the biological indicator 30. The incubation medium may be referred to as a growth medium. The incubation medium may be in the form of a solid or a liquid. The incubation medium may comprise a buffered aqueous solution although an advantage of the disclosed technology is that the buffer capacity of the incubation medium may be reduced so that the biological indicator may be more sensitive to pH shifts, redox potentials, enzymatic activity, and the like. Any procedure whereby the biological indicator is brought into contact with the incubation medium under conditions which allow for growth of the test organism, if it still exists, may be used. The incubation medium may be present in the sterilization chamber in powder or tablet form and, after sterilization, sterile water may be added such that the biological indicator comes into contact with the aqueous incubation medium.

The incubation medium may comprise one or more nutrient sources. The nutrient source may be used to provide energy for the growth of any of the test organisms that may survive the sterilization process. Examples of the nutrient sources may include pancreatic digest of casein, enzymatic digest of soybean meal, sucrose, dextrose, yeast extract, L-cystine, and mixtures of two or more thereof. A microbial growth indicator, which changes color or native state, in the presence of viable test organisms may be used with the incubation medium. The growth indicator may be dispersed or solubilized in the incubation medium and impart an initial color to the incubation medium. The growth indicator may also impart a color change in the incubation medium upon microorganism growth. Growth indicators which may be employed include pH-sensitive dye indicators (such as bromothymol blue, bromocresol purple, phenol red, etc. or combinations thereof), oxidation-reduction dye indicators (such as methylene blue, etc.), enzyme substrates, or mixtures of two or more thereof. The enzyme substrate may comprise any enzyme substrate whose activity correlates with one or more enzymes that may be present in the test organism. The enzyme substrates that may be used may include those discussed below. The use of these microbial growth indicators may result in a change in color in response to a phenomenon of microorganism growth, such as changes in pH, oxidation-reduction potentials, enzymatic activity, as well as other indications of growth. The incubation medium may further comprise one or more pH buffers, one or more neutralizers, one or more agents for maintaining osmotic equilibrium, or a mixture of two or more thereof. The pH buffers may include $K_2HPO_4$, $KH_2PO_4$, $(NH_4)_2HPO_4$, 2,2-Bis(hydroxylmethyl)-2,2',2"-nitrilothiethanol (Bis Tris), 1,3-Bis[tris(hydroxymethyl)methylamino]propane (Bis-Tris Propane), 4-(2-Hydroxyethyl)piperazine-ethanesulfonic acid (HEPES), 2-Amino-2-(hydroxymethyl)-1,3-propanediol (Trizma, Tris base), N -[Tris(hydroxymethyl)methyl]glycine (Tricine), Diglycine (Gly-Gly), N,N-Bis(2-hydroxyethyl)glycine (Bicine), N-(2-Acetamido)iminodiacetic acid (ADA), N-(2-Acetamido)-2-aminoethanesulfonic acid (aces), 1,4-piperazinediethanesulfonic acid (PIPES), β-Hydroxy-4-morpholinepropanesulfonic acid (MOPSO), N,N-Bis (2-hydroxyethyl)-2-aminoethanesulfonic acid (BES), 3-(N-Morpholino)propanesulfonic acid (MOPS), 2-[(2-Hydroxy-1,1-bis(hydroxylmethyl)ethyl)amino]ethanesulfonic acid (TES), 3-(N,N-Bis[2-hydroxyethyl]amino)-2-hydroxypropanesulfonic acid (DIPSO), 4-(N-Morpholino)butanesulfonic acid (MOBS), 2-Hydroxy-3-[tris(hydroxymethyl)methylamino]-1-propanesulfonic acid (TAPSO), 4-(2-Hydroxyethyl)piperazine-1-(2-hydroxypropanesulfonic acid hydrate (HEPPSO), piperazine-1,4-bis(2-hydroxypropanesulfonic acid) dihydrate (POPSO), 4-(2-Hydroxyethyl)-1-piperazine propanesulfonic acid (EPPS), N-(2-Hydroxyethyl)piperazine-N'-(4-butanesulfonic acid) (HEPBS), [(2-Hydroxy-1,1-bis(hydroxymethyl)ethyl)amino]-1-propanesulfonic acid (TAPS), 2-Amino-2-methyl-1,3-propanediol (AMPD), N-tris(Hydroxymethyl)methyl-4-aminobutanesulfonic acid (TABS), N-(1,1-Dimethyl-2-hydroxyethyl)-3-amino-2-hydroxypropanesulfonic acid (AMPSO), 2-(Cyclohexylamino)ethanesulfonic acid (CHES), 3-(Cyclohexylamino)-2-hydroxyl-1-propanesulfonic acid (CAPSO), 2-Amino-2-methyl-1-propanol (AMP), 3-(Cyclohexylamino)-1-propanesulfonic acid (CAPS), 4-(Cyclohexylamino)-1-butanesulfonic acid (CABS), 2-(N-Morpholino)ethanesulfonic acid hydrate (MES), N-(2-Acetamido)-2-aminoethanesulfonic acid (ACES), and mixtures of two or more thereof. The neutralizers may include but are not limited to sodium thioglycollate, sodium thiosulfate, catalase, sodium bisulfate, sodium bisulfite lecithin, polysorbate 20, polysorbate 80, calcium bicarbonate, and mixtures of two or more thereof. The agents for maintaining osmotic equilibrium may include sodium salt, potassium salts, magnesium salts, manganese salts, calcium salts, metallic salts, sodium chloride, potassium chloride, magnesium sulfate, iron chloride, and mixtures of two or more thereof. The incubation medium may comprise an aqueous composition comprising: water; from about 0.01 to about 100 grams per liter of water (g/l), and in one embodiment from about 0.1 to about 50 g/l, of one or more nutrient sources; from about $1.0 \times 10^{-5}$ to about 10 g/l, and in one embodiment from about $1.0 \times 10^{-4}$ to about 1.0 g/l of one or more microbial growth indicators; up to about 5000 g/l, and in one embodiment from about 0.001 to about 5000 g/l, and in one embodiment from about 0.1 to about 1000 g/l, of one or more pH buffers; up to about 100 g/l, and in one embodiment from about 0.01 to about 100 g/l, and in one embodiment from about 0.1 to about 50 g/l, of one or more neutralizers; up to about 50 g/l, and in one embodiment from about 0.1 to about 50 g/l, and in one embodiment from about 0.1 to about 25 g/l, of one or more agents for maintaining osmotic equilibrium.

The incubation medium may have a relatively low buffering capacity in the range from about −0.001 to about −0.070 mol $H^+$, and in one embodiment in the range from about −0.01 to about −0.070 mol $H^+$, and in one embodiment in the range from about −0.01 to about −0.014 mol $H^+$. This buffering capacity may be provided by formulating the incubation medium with the indicated low buffering capacity or by diluting a pre-formulated incubation medium having a higher buffering capacity with water or other liquid. In the prior art, incubation media have typically been formulated to enhance the growth of organisms. This may cause the organisms to expend more energy on growth and division and less energy on pumping out accumulating acidic waste and other by-products produced by metabolism. The buffers within an incubation medium may be used to keep the medium sufficiently neutral or alkaline to facilitate the transport of acidic by-products (protons) across the cell membrane. The incubation medium used with the disclosed sterilization indicator may focus on how rapidly growth may be detected. By employing a reduced buffering capacity in the range from about −0.001 to about −0.010 mol $H^+$, and in one embodiment in the range from about −0.005 to about −0.007 mol $H^+$, the incubation medium may be more sensitive to small shifts in pH, redox potentials and/or enzymatic activity.

The incubation medium may comprise a nutrient broth, D/E neutralizing broth, Davis minimal medium, sterility test broth, as well as any soybean-casein digest or beef extract based media. These may include an aqueous solution of soybean-casein digest broth, fluid thioglycollate and Dextrose Tryptone (Difco Laboratories, Inc.). A modified tryptic soy broth base, without glucose, may be used. If enzymatic activity is being measured, the incubation medium may comprise water, an enzyme substrate, and optionally pH buffers.

An example of an incubation medium that may be used is Bacto™ Tryptic Soy Broth which contains pancreatic digest of casein (17.0 g/l), enzymatic digest of soybean meal (3.0 g/l), sodium chloride (5.0 g/l), dipotassium phosphate (2.5 g/l), and dextrose (2.5 g/l). These ingredients may be dispersed or dissolved in water. The concentrations expressed in terms of g/l refer to grams of ingredient per liter of water. Pancreatic digest of casein, enzymatic digest of soybean meal, and dextrose provide energy sources for growth of the microorganism. These may be referred to as nutrient sources. Sodium chloride may be used to maintain an osmotic equilibrium in the liquid medium. Dipotassium phosphate may act as a pH buffer. Phenol red, for example, which is a pH-sensitive dye, may be added (18 mg/l) to the Bacto™ Tryptic Soy Broth formulation. The dye may be useful as an indicator of pH shift in the incubation medium resulting from microorganism growth.

Another example of an incubation medium that may be used is BBL™ Fluid Thioglycollate Medium. This incubation medium contains pancreatic digest of casein (15.0 g/l), yeast extract (5.0 g/l), dextrose (5.5 g/l), sodium chloride (2.5 g/l), L-cystine (0.5 g/l), sodium thioglycollate (0.5 g/l), and resazurin (1.0 mg/l). These ingredients may be dispersed or dissolved in water. The pancreatic digest of casein, yeast extract, dextrose, and L-cystine are nutrient sources which may provide energy for microorganism growth. The sodium chloride may be used to maintain osmotic equilibrium in the incubation medium. Sodium thioglycollate may be used as a neutralizer. Resazurin may be used as an oxidation/reduction dye indicator. Other nutrient sources, osmotic mediators and general ingredients known to those practiced in the art may be substituted for listed ingredients.

An advantage of the disclosed technology is that the size of the biological indicator 30 may be relatively small and thus the volume of incubation medium needed to incubate any surviving test organisms on the carrier 12 may be relatively small. This may result in an incubation period that may be relatively short. Thus, in one embodiment, the biological indicator 30 may be supported by a carrier 12 that is relatively small, the carrier 12 having a surface area in the range from about 1 to about 80 $mm^2$, and in one embodiment from about 5 to about 50 $mm^2$. The number of spores supported by the carrier 12, before sterilization, may be in the range from about $10^4$ to about $10^7$ cfu/$mm^2$, and in one embodiment in the range from about $10^5$ to about $10^6$ cfu/$mm^2$. The volume of incubation medium needed to incubate the biological indicator 30 after sterilization may be in the range from about 0.1 to about 5 ml, and in one embodiment from about 0.1 to about 4 ml, and in one embodiment from about 0.1 to about 3 ml, and in one embodiment from about 0.1 to about 2 ml, and in one embodiment from about 0.1 to about 1.5 ml, and in one embodiment from about 0.3 to about 1 ml. The time required to incubate the biological indicator 30 after sterilization may be in the range from about 0.1 to about 48 hours, and in one embodiment from about 0.1 to about 36 hours, and in one embodiment from about 0.1 to about 24 hours, and in one embodiment from about 0.1 to about 18 hours, and in one embodiment from about 0.1 to about 15 hours, and in one embodiment from about 0.1 to about 12 hours, and in one embodiment from about 0.1 to about 10 hours, and in one embodiment from about 0.1 to about 8 hours, and in one embodiment from about 0.1 to about 6 hours, and in one embodiment from about 0.1 to about 5 hours, and in one embodiment from about 0.1 to about 4 hours.

The enzyme that may be used as the biological indicator 30 may comprise any enzyme, including extracellular or intracellular enzymes, whose activity may correlate with the viability of at least one test organism. By "correlate" it is meant that the enzyme activity, over background, may be used to predict future growth of a test organism. The enzyme may be one which following a sterilization cycle, which is sublethal to the test organism, remains sufficiently active to react with an enzyme substrate within a desired period of time, for example, from about 4 to about 164 hours, and in one embodiment from about 4 to about 84 hours, yet be inactivated or appreciably reduced in activity following a sterilization which would be lethal to the test organism.

The following test may be useful in identifying those enzymes having the requisite characteristics to be useful as the biological indicator 30. The enzyme when subjected to sterilization conditions which would be just sufficient to decrease the population of about $1 \times 10^6$ test organisms by about 6 logs (i.e., to a population of about zero as measured by lack of outgrowth of the test organisms), may have residual enzyme activity which is equal to "background" as measured by reaction with an enzyme substrate; however, the enzyme upon being subjected to sterilization conditions sufficient only to decrease the population of about $1 \times 10^6$ test organisms by at least about 1 log, but less than about 6 logs, may have enzyme activity greater than "background" as measured by reaction with the enzyme substrate. The enzyme substrate may be a substance, or mixture of substances, which when acted upon by the enzyme produces a detectable, e.g., fluorescent or colored, enzyme-modified product. The enzyme activity may be measured by the amount of detectable enzyme-modified product produced. The enzyme may be one which has sufficient activity, following sterilization conditions insufficient to decrease the population of the test organism by about 6 logs, to react with the enzyme substrate and produce a detectable amount of enzyme-modified product within a period of time in the range from about 0.1 to about 48 hours, and in one embodiment in the range from about 0.1 to about 12 hours, and in one embodiment in the range from about 0.1 to about 4 hours.

The activity of the biological indicator 30 after sterilization conditions that are insufficient to decrease the microorganism population by about 6 logs, may be at least about 2 percent greater than background, and in one embodiment at least about 5 percent greater than background, and in one embodiment at least about 10 percent greater than background. The residual enzyme activity level which is defined as "background" may be higher than that achieved by the spontaneous conversion of enzyme substrate to product after the enzyme has been inactivated.

Enzymes which may be used in the biological indicator 30 may include, but not limited to, hydrolytic enzymes from spore-forming microorganisms. These enzymes may include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, and a fatty acid esterase, derived from spore-forming microorganisms, such as *Candida, Bacillus* or *Clostridium* species of microorganisms.

Enzymes from *Geobacillus stearothermophilus* that may be used may include alpha-D-glucosidase, beta-D-glucosidase, alkaline phosphatase, acid phosphatase, butyrate esterase, caprylate esterase lipase, leucine aminopeptidase, chymotrypsin, phosphohydrolase, alpha-D-galactosidase, beta-D-galactosidase, alanine aminopeptidase, tyrosine aminopeptidase, and phenylalanine aminopeptidase and a fatty acid esterase. Enzymes from *Bacillus subtilis* that may be used include alpha-L-arabinofuranosidase, beta-D-glucosidase, N-acetyl-beta-glucosaminidase, beta-D-cellobiosidase, alanine aminopeptidase, proline aminopeptidase, tyrosine aminopeptidase, leucine aminopeptidase and phenylalanine aminopeptidase.

Beta-D-glucosidase and alpha-L-arabinofuranosidase from *Bacillus subtilis* may be used in the monitoring of ethylene oxide sterilization. Alpha-D-glucosidase from *Geobacillus stearothermophilus* may be used to monitor steam sterilization conditions.

An enzyme substrate may be a substance or mixture of substances which when acted upon by an enzyme is converted into an enzyme-modified product. In general, the enzyme-modified product may be a luminescent, fluorescent, colored or radioactive material. However, the enzyme substrate may comprise one or more compounds which when acted upon by the enzyme, may yield a product which reacts with an additional compound or composition to yield a luminescent, fluorescent, colored or radioactive material. When the enzyme substrate is to be included in the biological indicator 30 during sterilization, the enzyme substrate should not spontaneously break down or convert to a detectable product during sterilization or incubation. For example, in sterilization indicators used to monitor steam and dry heat sterilization, the enzyme substrate should be stable at temperatures between about 20° C. and about 180° C. Where the enzyme substrate is to be included with a conventional incubation medium, it should be stable in the incubation medium, e.g., not autofluoresce in the incubation medium.

There are two basic types of enzyme substrates that may be used for the detection of specific enzymes. The first type of enzyme substrate may be either fluorogenic or chromogenic, and may be given a chemical formula such as, AB. When acted upon by the enzyme, AB, may break down to A+B. B, for example, may be either fluorescent or colored. A specific example of a fluorogenic substrate of this type may be 4-methylumbelliferyl phosphate. In the presence of the enzyme phosphatase, the substrate may be broken down into 4-methylumbelliferone and phosphate. Other fluorogenic substrates of this type may include the derivatives of 4-methylumbelliferyl, resorufin, and fluorescein. An example of a chromogenic substrate of this type may be 5-bromo-4-chloro-3-indolyl phosphate. In the presence of phosphatase, the substrate may be broken down into indigo blue and phosphate. Other chromogenic substrates of this type may include derivatives of indoxyl, nitrophenol and phenolphthalein, where chromogenic indoxyl substrates may be broken down and a calorimetric response produced by the following chemical reaction, AB. When subsequently acted upon by the appropriate enzyme, AB, may break down to A+B. The color may then be obtained when BB occurs.

The second type of enzyme substrate may be given the chemical formula CD, for example, which may be converted by a specific enzyme to C+D. However, neither C nor D may be fluorescent or colored, but D may be capable of being further reacted with compound Z to give a fluorescent or colored compound, thus indicating enzyme activity. A specific fluorogenic example of this type may be the amino acid lysine. In the presence of the enzyme lysine decarboxylase, lysine may lose a molecule of $CO_2$. The remaining part of the lysine may then be called cadaverine, which is strongly basic. A basic indicator such as 4-methylumbelliferone may be incorporated and may fluoresce in the presence of a strong base. A chromogenic substrate of this type may be 2-naphthyl phosphate. The enzyme phosphatase, may react with the enzyme substrate to yield beta-naphthol. The liberated beta-naphthol may react with a chromogenic reagent containing 1-diazo-4-benzoylamino-2,5-diethoxybenzene to produce a violet color.

The enzyme substrate may be a fluorogenic compound, defined herein as a compound capable of being enzymatically modified, e.g., by hydrolysis, to provide a derivative fluorophor which has an appreciably modified or increased fluorescence.

The fluorogenic compounds may in themselves be either non-fluorescent or meta-fluorescent (i.e., fluorescent in a distinctly different way, e.g., either by color or intensity, than the corresponding enzyme-modified products) and appropriate wavelengths of excitation and detection, may be used to separate the fluorescence signal developed by the enzyme modification from any other fluorescence that may be present.

A number of enzyme substrates for enzymes of diverse origins, either naturally occurring or synthetic in origin, may be used. These may include fluorogenic 4-methylumbelliferyl derivatives (hydrolyzable to 4-methylumbelliferone); derivatives of 7-amido-4-methyl-coumarin; diacetylfluorescein derivatives; and fluorescamine.

Derivatives of 4-methylumbelliferyl that may be used as the enzyme substrate may include: 4-methylumbelliferyl-2-acetamido-4,6-O-benzylidene-2-deoxy-beta-D-lucopyranoside; 4-methylumbelliferyl acetate; 4-methylumbelliferyl-N-acetyl-beta-D-galactosaminide; 4-methylumbelliferyl-N-acetyl-alpha-D-glucosaminide; 4-methylumbelliferyl-N-acetyl-beta-D-glucosaminide; 2'-(4-methylumbelliferyl)-alpha-D-N-acetyl neuraminic acid; 4-methylumbelliferyl-alpha-L-arabinofuranoside; 4-methylumbelliferyl alpha-L-arabinoside; 4-methylumbelliferyl butyrate; 4-methylumbelliferyl-beta-D-cellobioside; methylumbelliferyl-beta-D-N,N'-diacetyl chitobioside; 4-methylumbelliferyl elaidate; 4-methylumbelliferyl-beta-D-fucoside; 4-methylumbelliferyl-alpha-L-fucoside; 4-methylumbelliferyl-beta-L-fucoside; 4-methylumbelliferyl-alpha-D-galactoside; 4-methylumbelliferyl-beta-D-galactoside; 4-methylumbelliferyl-alpha-D-glucoside; 4-methylumbelliferyl-beta-D-glucoside; 4-methylumbelliferyl-beta-D-glucuronide; 4-methylumbelliferyl p-guanidinobenzoate; 4-methylumbelliferyl heptanoate; 4-methylumbelliferyl-alpha-D-mannopyranoside; 4-methylumbelliferyl-beta-D-mannopyranoside; 4-methylumbelliferyl oleate; 4-methylumbelliferyl palmitate; 4-methylumbelliferyl phosphate; 4-methylumbelliferyl propionate; 4-methylumbelliferyl stearate; 4-methylumbelliferyl sulfate; 4-methylumbelliferyl-beta-D-N,N',N''-triacetylchitotriose; 4'-methylumbelliferyl 2,3,5-tri-beta-benzoyl-alpha-L-arabinofuranoside; 4-methylumbelliferyl-beta-trimethylammonium cinnamate chloride; and 4-methylumbelliferyl-beta-D-xyloside.

Derivatives of 7-amido-4-methylcoumarin that may be used as the enzyme substrate may include: L-alanine-7-amido-4-methylcoumarin; L-proline-7-amido-4-methylcoumarin; L-tyrosine-7-amido-4-methylcoumarin; L-leucine-7-amido-4-methylcoumarin; L-phenylalanine-7-amido-4-methylcoumarin; and 7-glutaryl-phenylalanine-7-amido-4-methylcoumarin.

Peptide derivatives of 7-amido-4-methyl coumarin that may be used as the enzyme substrate may include: N-t-BOC-Ile-Glu-Gly-Arg 7-amido-4-methylcoumarin; N-t-BOC-Leu-Ser-Thr-Arg 7-amido-4-methylcoumarin; N-CBZ-Phe-Arg 7-amido-4-methylcoumarin; Pro-Phe-Arg 7-amido-4-methylcoumarin; N-t-BOC-Val-Pro-Arg 7-amido-4-methylcoumarin; and N-glutaryl-Gly-Arg 7-amido-4-methylcoumarin.

Derivatives of diacetylfluorescein that may be used as the enzyme substrate may include fluorescein diacetate, fluorescein di-(beta-D-galacto-pyranoside), and fluorescein dilaurate.

Where the enzyme whose activity is to be detected is alpha-D-glucosidase, chymotrypsin, or fatty acid esterase, e.g., from *Geobacillus stearothermophilus*, a fluorogenic enzyme substrate that may be used may be 4-methylumbelliferyl-alpha-D-glucoside, 7-glutarylphenylalanine-7-amido-4-methyl coumarin, or 4-methylumbelliferyl heptanoate, respectively. Where the enzyme whose activity is to be detected is alpha-L-arabinofuranosidase, e.g., derived from *Bacillus subtilis*, a fluorogenic enzyme substrate that may be used may be 4-methylumbelliferyl-alpha-L-arabinofuranoside. Where the enzyme whose activity is to be detected is beta-D-glucosidase, e.g., derived from *Bacillus subtilis*, a fluorogenic enzyme substrate that may be used may be 4-methylumbelliferyl-beta-D-glucoside.

An enzyme substrate that may be used may be a chromogenic compound capable of being enzymatically modified to give a derivative chromophor, or a product which reacts with another compound of a like or different kind to give a derivative chromophor, which chromophor has a different or more intense color. The chromogenic compounds may be non-colored or colored in a distinctly different way, e.g., either by color or intensity, than the corresponding enzyme-modified products. These changes may be discernible by eye or require the use of color detecting instrumentation. Appropriate wavelengths of excitation and detection, in manners well known to users of colorometric instrumentation, may be used to separate the colored signal developed by the enzyme modification from any other color that may be present.

Chromogenic compounds that may be used as enzyme substrates that may be used may include 5-bromo-4-chloro-3-indolyl derivatives; nitrophenyl derivatives; indoxyl derivatives; and phenolphthalein derivatives.

Derivatives of 5-bromo-4-chloro-3-indolyl that may be used may include 5-bromo-6-chloro-3-indolyl acetate, 5-bromo-4-chloro-3-indolyl acetate, 5-bromo-4-chloro-3-indoxyl-beta-D-galactopyranoside, 5-bromo-4-chloro-3-indolyl-1,3-diacetate, 5-bromo-4-chloro-3-indolyl-beta-D-fucopyranoside, 5-bromo-4-chloro-3-indolyl-beta-D-glucopyranoside, 5-bromo-4-chloro-3-indolyl-beta-D-glucuronic acid, 5-bromo-4-chloro-3-indolyl phosphate, and 5-bromo-4-chloro-3-indolyl sulfate.

Derivatives of nitrophenyl that may be used may include p-nitrophenol and o-nitrophenol derivatives. These include diethyl-p-nitrophenyl phosphate; di-p-nitrophenyl phosphate; p-nitrophenyl-2-acetamido-2-deoxy-3-O-beta-galactopyranosyl-beta-glucopyranoside; p-nitrophenyl-2-acetamido-2-deoxy-beta-glucopyranoside; p-nitrophenyl acetate; p-nitrophenyl-N-acetyl-beta-D-glucosaminide; p-nitrophenyl-beta-D-N,N'-diacetylchitobioside; p-nitrophenyl-alpha-glucopyranoside; p-nitrophenyl-alpha-maltoside; p-nitrophenyl-beta-maltoside; p-nitrophenyl-alpha-mannopyranoside; p-nitrophenyl-beta-mannopyranoside;

p-nitrophenyl myristate; p-nitrophenyl palmitate; p-nitrophenyl phosphate; bis(p-nitrophenyl)phosphate; tris(p-nitrophenyl)phosphate; p-nitrophenyl-beta-glucopyranoside; p-nitrophenyl-beta-glucuronide; alpha-p-nitrophenylglycerine; p-nitrophenyl-alpha-rhamnopyranoside; p-nitrophenyl stearate; p-nitrophenyl sulfate; p-nitrophenyl-2,3,4,6-tetra-O-acetyl-beta-glucosaminide; p-nitrophenyl thymidine monophosphate; p-nitrophenyl-2,3,4-tri-O-acetyl-beta-glucuronic acid methyl ester; and p-nitrophenyl valerate.

Useful o-nitrophenols may include o-nitrophenyl acetate, o-nitrophenyl-beta-glucoside and o-nitrophenyl-beta-D-glucopyranoside. Other useful nitrophenyl derivatives may include nitrophenyl-beta-fucopyranoside; nitrophenyl-alpha-galactopyranoside; nitrophenyl-beta-galactopyranoside; nitrophenyl butyrate; nitrophenyl caprate; nitrophenyl caproate; nitrophenyl caprylate; nitrophenyl laurate; and nitrophenyl propionate.

Indoxyl derivatives that may be used may include indoxyl-acetate; indoxyl beta-D-glucoside; 3-indoxyl sulfate; and 3-indoxyl phosphate.

Phenolphthalein derivatives that may be used may include: phenolphthalein dibutyrate; phenolphthalein diphosphate; phenolphthalein disulfate; phenolphthalein glucuronic acid; phenolphthalein mono-beta-glucosiduronic acid; phenolphthalein mono-beta-glucuronic acid; and phenolphthalein mono-phosphate.

The above-described chromogenic enzyme substrates may react directly with an appropriate enzyme to produce a chromophor.

Additional enzyme substrates containing 1-naphthyl, 2-naphthyl and Napthyl-AS-BI derivatives may be employed if the derivative enzyme modified product is further reacted with a chromogenic reagent, such as diazotized dyes, e.g., 1-diazo-4-benzoylamino-2,5-diethoxybenzene, 1-diazo-4-benzoylamino-2, 5-diethoxybenzene, p-diazo-2,5-diethoxy-N-benzoyalanine, 4-chloro-2-methylbenzene diazonium chloride, and o-aminoazotoluene diazonium salt, to produce a chromophor.

Derivatives of 1-napthyl that may be used may include 1-naphthyl-N-acetyl-beta-D-glucosaminide.

Derivatives of 2-naphthyl that may be used may include 2-naphthyl-phosphate; 2-naphthyl-butyrate; 2-naphthyl-caprylate; 2-naphthyl-myristate; L-leucyl-2-naphthylamide; L-valyl-2-naphthylamide; L-cystyl-2-naphthylamide; N-benzoyl-DL-arginine-2-naphthylamide; N-glutaryl-phenylalanine 2-naphthyl-amine; 2-naphthyl-phosphate; 6-Br-2-naphthyl-alpha-D-galacto-pyranoside; 2-naphthyl-beta-D-galacto-pyranoside; 2-naphthyl-2-D-glucopyranoside; 6-bromo-2-naphthol-beta-D-glucopyranoside; 6-bromo-2-naphthyl-2-D-mannopyranoside; and 2-naphthyl-alpha-L-fucopyranoside.

Derivatives of naphthyl-AS-BI that may be used may include naphthyl-AS-BI-phosphate; and naphthyl-AS-BI-beta-D-glucuronide.

Where the enzyme whose activity is to be detected is alpha-D-glucosidase, e.g., from *Geobacillus stearothermophilus*, the enzyme substrate may be p-nitrophenyl-alpha-glucopyranoside. Where the enzyme whose activity is to be detected is alpha-L-arabinofuranosidase, e.g., derived from *Bacillus subtilis*, the enzyme substrate that may be used may be p-nitrophenyl-alpha-L-arabinofuranoside. Where the enzyme whose activity is to be detected is beta-D-glucosidase, e.g., derived from *Bacillus subtilis*, the enzyme substrate that may be used may be p-nitrophenyl-beta-D-glucopyranoside. Where the enzyme whose activity is to be detected is β-galactosidase, the enzyme substrate may be 5-bromo-4-chloro-3-indolyl-β-D-galactopyranoside. Where the enzyme whose activity is to be detected is β-galactosidase, the enzyme substrate may be 4-methylumbelliferone-β-D-galactopyranoside.

The enzyme substrate that may be used may depend upon the identity of the enzyme whose activity is under study. Below is a list of a number of enzyme substrates and corresponding enzymes which may react with the substrate to produce a product having appreciably modified or increased fluorescence or color.

| Enzyme Substrate | Enzyme |
| --- | --- |
| 4-Methylumbelliferyl acetate | Esterase |
| 4-Methylumbelliferyl butyrate | Esterase |
| 4-Methylumbelliferyl elaidate | Lipase |
| 4-Methylumbelliferyl-β-D-galactopyranoside | β-D-Galactosidase |
| 4-Methylumbelliferyl-α-D-galactopyranoside | α-D-Galactosidase |
| 4-Methylumbelliferyl-α-D-glucopyranoside | α-D-Glucosidase |
| 4-Methylumbelliferyl-β-D-glucopyranoside | β-D-Glucosidase |
| 4-Methylumbelliferyl heptanoate | Esterase |
| 4-Methylumbelliferyl oleate | Lipase |
| 4-Methylumbelliferyl phosphate | Acid or Alkaline Phosphatase |
| 4-Methylumbelliferyl propionate | Esterase |
| 4-Methylumbelliferyl-β-D-galactoside | β-D-Galactosidase |
| 4-Methylumbelliferyl-β-D-glucoside | β-D-Glucosidase |
| 4-Methylumbelliferyl-α-D-glucoside | α-D-Glucosidase |
| 4-Methylumbelliferyl-α-L-arabinofuranoside | α-L-Arabinofuranosidase |
| L-Leucine-7-amido-4-methylcoumarin | Leucine aminopeptidase |
| 7-glutaryl-phenylalanine-7-amido-4-methylcoumarin | Chymotrypsin |
| D-Melibiose | α-D-Galactosidase |
| p-Nitrophenyl phosphate | Alkaline or Acid phosphatase |
| p-Nitrophenyl acetate | Lipase |
| o-Nitrophenyl-β-D-galactopyranoside | β-D-Galactosidase |
| p-Nitrophenyl-α-D-galactopyranoside | α-D-Galactosidase |
| o-Nitrophenyl-β-D-glucopyranoside | β-D-Glucosidase |
| p-Nitrophenyl-α-D-glucopyranoside | α-D-Glucosidase |
| p-Nitrophenyl-β-D-glucuronide | β-D-Glucuronidase |
| p-Nitrophenyl-α-L-arabinofuranoside | α-L-Arabinofuranosidase |
| p-Nitrophenyl laurate | Esterase |
| p-Nitrophenyl myristate | Esterase |
| p-Nitrophenyl palmitate | Esterase |
| p-Nitrophenyl phosphate diNa salt | Alkaline Phosphatase |
| Phenolphthalein dibutyrate | Esterase |
| Phenolphthalein diphosphate | Acid or Alkaline phosphatase |
| Phenolphthalein diphosphate pentaNa salt | Acid or Alkaline phosphatase |
| Phenolphthalein-β-D-glucuronide Na salt | β-D-Glucuronidase |
| Phenolphthalein-β-D-glucuronide | β-D-Glucuronidase |
| L-Phenylalanine ethylester HCl | Chymotrypsin |
| Phenyl-β-D-galactopyranoside | β-D-Galactosidase |
| Phenyl-β-D-glucuronide | β-D-Glucuronidase |
| Phenyl-β-D-glucopyranoside | β-D-Glucosidase |
| Phenyl-β-D-glucuronide | β-D-Glucuronidase |
| Phenyl-α-D-glucoside | α-D-Glucosidase |
| Sodium β-glycerophosphate | Acid or Alkaline phosphatase |
| Sodium 1-naphthyl phosphate | Acid or Alkaline phosphatase |
| Sodium 2-naphthyl phosphate | Acid or Alkaline phosphatase |
| 2-Naphthyl-butyrate | Esterase |
| β-Naphthyl acetate | Lipase |
| 6-Br-2-naphthyl-β-D-glucoside | β-D-Glucosidase |
| L-Leucyl-2-naphthylamide aminopeptidase | Leucine |
| L-Valyl-2-naphthylamide aminopeptidase | Valine |
| N-glutaryl-phenylalanine-2-naphthylamine | Chymotrypsin |
| Naphthyl-AS-BI-phosphate | Phosphohydralase |
| Indoxyl acetate | Lipase |
| N-Methylindoxyl acetate | Lipase |
| N-Methylindoxyl myristate | Lipase |
| 5-Bromoindoxyl acetate | Lipase |
| 3-Indoxyl phosphate | Acid or Alkaline phosphatase |
| Indoxyl-β-D-glucoside | β-D-Glucosidase |
| 5-Br-4-Cl-3-Indolyl acetate | Lipase |
| 5-Br-4-Cl-3-Indolyl phosphate | Alkaline or Acid phosphatase |

-continued

| Enzyme Substrate | Enzyme |
| --- | --- |
| 5-Br-4-Cl-3-Indolyl-β-D-glucuronic acid | β-D-Glucuronidase |
| Diacetylfluorescein | Lipase/esterase |

After the sterilization process has been completed, the carrier 12 with any enzyme that may have survived the sterilization process on it may be contacted with or placed in an aqueous medium or aqueous solution or on a semi-solid or solid containing an appropriate enzyme substrate. The aqueous medium or aqueous solution may be buffered. An advantage of the disclosed technology is that the amount of enzyme positioned on the carrier 12 may be relatively small, and thus the volume of the enzyme substrate needed to detect any enzymes that may have survived sterilization may be relatively small. This may result in a detection period that may be relatively short. The carrier 12 may have a surface area in the range from about 1 to about 80 mm$^2$, and in one embodiment in the range from about 5 to about 50 mm$^2$. The units of enzyme supported by the carrier 12, before sterilization, may be in the range from about $10^{-7}$ to about $10^6$ units/mm$^2$, and in one embodiment in the range from about $10^{-4}$ to about $10^3$ units/mm$^2$. The enzyme and its appropriate enzyme substrate may contact each other in the aqueous medium or aqueous solution. An isotonic buffer, such as phosphate buffered saline solution, tris(hydroxymethyl)aminomethane-HCl solution, or acetate buffer may be used. These isotonic buffers may be compatible with most fluorogenic and chromogenic enzyme substrates. Another consideration in choosing the buffer is its influence on the enzyme activity. For example, phosphate buffered saline contains a high concentration of inorganic phosphate which is a strong competitive inhibitor of alkaline phosphatase. For this enzyme, a tris-HCl buffer may be used.

The concentration of enzyme substrate in the buffered aqueous solution may be dependent upon the identity of the enzyme substrate and the enzyme, the amount of enzyme-modified product that must be generated to be detectable, either visually or by instrument, and the amount of time required to determine whether active enzyme is present in the reaction mixture. The amount of enzyme substrate that may be sufficient may be the amount needed to react with any active enzyme that may be present after the sterilization has been completed such that an enzyme-modified product at a molar concentration of at least about $1\times10^{-8}$ molar may be produced within a period of up to about 4 hours or less. Where the enzyme substrate is a 4-methylumbelliferyl derivative, its concentration in the buffered aqueous solution may be in the range from about $1\times10^{-5}$ to about $1\times10^{-3}$ molar.

The pH of the buffered aqueous solution containing the enzyme substrate may be adjusted to a pH in the range from about 5 to about 9.5, and in one embodiment about 7.5, in order to prevent autofluorescence for some basic fluorogenic substrates.

The enzyme substrate in the aqueous buffered solution may be incubated with the enzyme whose activity is to be detected after the enzyme has been subjected to the sterilization cycle. Incubation may be continued for a period of time and under conditions sufficient to liberate a detectable amount of the enzyme-modified product, assuming that any of the enzyme remains active. In general, the amount of product which may be detectable may be as low as about $1\times10^{-8}$ molar. The incubation conditions should be sufficient to generate at least about $1\times10^{-8}$ molar of enzyme-modified product, and in one embodiment from about $1\times10^{-6}$ to about $1\times10^{-5}$ molar of enzyme-modified product. The incubation time and temperature needed to produce a detectable amount of enzyme-modified product may depend upon the identity of the enzyme and the enzyme substrate, and the concentrations of each present in the buffered aqueous solution. In general, the incubation time required may be up to about 48 hours, and in one embodiment up to about 36 hours, and the incubation temperature may be in the range from about 20° C. to about 70° C. The incubation time may be in the range from about 0.1 to about 48 hours, and in one embodiment in the range from about 0.1 to about 36 hours, and in one embodiment in the range from about 0.1 to about 24 hours, and in one embodiment in the range from about 0.1 to about 12 hours, and in one embodiment in the range from about 0.1 to about 6 hours, and in one embodiment in the range from about 0.1 to about 4 hours, and in one embodiment in the range from about 0.1 to about 3 hours. Where *Bacillus subtilis* or *Geobacillus stearothermophilus* is the source of the enzyme, the incubation time may be in the range from about 0.1 to about 3 hours, and the incubation temperature may be in the range from about 30° C. to about 40° C., and in the range from about 50° C. to about 65° C., respectively.

Generally applicable methods for detecting the enzyme-modified product that may be used may include photometric, potentiometric, gravimetric, calorimetric, conductometric, or amperometric techniques. In one embodiment, fluorometric or spectrophotometric methods may be used. For example, the specific enzyme substrate may comprise a 4-methylumbelliferyl derivative which on interaction with the enzyme gives rise to umbelliferone which may be monitored fluorometrically, or the substrate may comprise a nitrophenol, or similar type of derivative, which on interaction with the enzyme gives rise to a product which may be monitored calorimetrically.

The biological indicator 30, although herein described primarily in terms of a single enzyme and/or test organism, may comprise a plurality of enzymes and/or test organisms or combinations thereof. For example, the biological indicator 30 may contain four types of enzymes (which may be derived from three types of microorganisms), one enzyme being resistant to heat, a second being resistant to gaseous sterilizing media, a third being resistant to radiation, e.g., gamma or beta irradiation, and a fourth being resistant to fluid based media, e.g., peracetic acid, stabilized hydrogen peroxide, chloramines, quaternary amines, phenols, ozone water, or gluteraldehyde, etc. Similarly, the biological indicator 30 may contain three species of test organisms, one species being resistant to heat, a second species being resistant to gaseous sterilizing media, and the third species being resistant to radiation and a fourth resistant to fluid based media.

Example 1

A sheet of Ahlstrom 238 paper (a paper product supplied by Ahlstrom) is cut into six circular support disks, each with a diameter of 6 mm (surface area of 28.3 mm$^2$). Three of the disks are inoculated on one side with 7 microliters of *Geobacillus stearothermophilus* spore suspension having a population greater than $10^8$ cfu per milliliter. Three of the disks are not inoculated. Each disk is sonic welded to a support strip of polystyrene having the dimensions of 25 mm×6 mm×0.25 mm. For each disk, a weld horn is brought into contact with one side of the carrier strip while the disk is placed in contact with the other side of the carrier strip. For the disks that are inoculated, the side of the disks not containing spores is placed in contact with the support strip. Following sonication, the three uninoculated disks are inoculated in the same manner as described above. FIG. 4 shows the results of these tests. These tests demonstrate a lack of significant microorganism loss as a result of sonic welding.

Example 2

Sterilization indicator samples of the type described in Example 1 are inoculated with $10^6$ cfu/ml of *Geobacillus stearothermophilus* and exposed to incubation media samples of different volumes and buffering capacities. The samples are monitored for pH change as a function of microorganism growth. The incubation media samples are as follows:

Sample A: 1.0 ml of Tryptic Soy Broth (TSB) with phenol red with full buffering capacity.

Sample B: 0.5 ml of TSB with phenol red and 0.5 ml of sterile deionized (DI) water with 50% of full buffering capacity.

Sample C: 0.4 ml of TSB with phenol red and 0.1 ml of sterile DI water with 80% of full buffering capacity.

Sample D: 0.3 ml of TSB with phenol red and 0.2 ml of sterile DI water with 60% full buffering capacity.

Sample E: 0.2 ml of TSB with phenol red and 0.3 ml of sterile DI water with 40% full buffering capacity.

The results are shown in FIG. 5. These results indicate that the smaller incubation media volumes and reduced buffering capacity show microbial growth more quickly than larger incubation media volumes.

While the disclosed technology has been explained in relation to specific embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A sterilization indicator, comprising:
a carrier, the carrier having a first surface and a second surface;
a support, the support having a first section and a second section, the carrier overlying the first section of the support, the second surface of the carrier being adhered to the first section of the support; and
a biological indicator supported by the carrier, the first section of the support having a length and the second section of the support having a length, the ratio of the length of the second section of the support to the length of the first section of the support being in the range from about 2:1 to about 12:1, the second section of the support being of sufficient dimension to function as a handle to permit handling the sterilization indicator without contacting the biological indicator;
the sterilization indicator being formed by applying the biological indicator to the carrier and then adhering the carrier to the support, the carrier being adhered to the support using sonic welding, the carrier having a surface area in the range from about 1 to about 80 mm², the volume of incubation medium needed to incubate the biological indicator being in the range from about 0.1 to about 5 ml, the time required to incubate the biological indicator being in the range from about 0.1 to about 48 hours,
wherein the sonic welding, when applied to the carrier with the biological indicator applied, exhibits no significant difference in the biological indicator following the sonic welding as compared to prior to the sonic welding, and wherein the biological indicator comprises *Geobacillus stearothermophilus*.

2. The sterilization indicator of claim 1 wherein the first surface of the carrier has a surface area in the range from about 5 to about 50 mm².

3. The sterilization indicator of claim 1 wherein the carrier comprises a porous material or a non-porous material.

4. The sterilization indicator of claim 1 wherein the carrier comprises paper, metal, glass, ceramic, plastic, membranes, or a combination of two or more thereof.

5. The sterilization indicator of claim 1 wherein the carrier comprises compressed fibers.

6. The sterilization indicator of claim 1 wherein the carrier comprises a porous material made of sintered glass, glass fibers, ceramic, synthetic polymer, or a combination of two or more thereof.

7. The sterilization indicator of claim 1 wherein the carrier comprises paper.

8. The sterilization indicator of claim 1 wherein the carrier comprises a cellulose pad.

9. The sterilization indicator of claim 1 wherein the carrier is in the form of a square, rectangle, oval, or prismatic cross-section.

10. The sterilization indicator of claim 1 wherein the support is made of a material comprising metal, glass, ceramic, plastic, or a combination of two or more thereof.

11. The sterilization indicator of claim 1 wherein the support is made of plastic.

12. The sterilization indicator of claim 1 wherein the support is made of polystyrene.

13. The sterilization indicator of claim 1 wherein the support is in the form of a rectangular strip with a length, the first section of the support comprising a minor part of the length of the support, the second section of the support comprising a major part of the length of the support.

14. The sterilization indicator of claim 1 wherein the biological indicator further comprises one or more additional test organisms, one or more enzymes, or a mixture thereof.

15. The sterilization indicator of claim 1 wherein the biological indicator comprises spores of *Geobacillus stearothermophilus*.

16. The sterilization indicator of claim 15 wherein the concentration of spores supported by the carrier is from about $10^4$ to about $10^7$ cfu per square millimeter of the carrier.

17. The sterilization indicator of claim 1 wherein the biological indicator further comprises *Bacillus atrophaeus, Bacillus subtilis, Bacillus pumilus, Bacillus coagulans, Clostridium sporogenes, Bacillus subtilis globigii, Bacillus cereus, Bacillus circulans*, or a mixture of two or more thereof.

18. The sterilization indicator of claim 1 wherein the biological indicator further comprises fungi, mycobacteria, protozoa, vegetative bacteria, or a mixture of two or more thereof.

19. The sterilization indicator of claim 1 wherein the biological indicator further comprises *Aspergillus niger, Candida albicans, Trichophyton mentagrophytes, Wangiella dermatitis, Mycobacterium chelonae, Mycobacterium gordonae, Mycobacterium smegmantis, Mycobacterium terrae, Giardia lamblia, Cryptosporidium parvum, Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Staphylococcus aureus, Staphylococcus epidermidis, Stenotrophomonas maltophilia*, or a mixture of two or more thereof.

20. The sterilization indicator of claim 1 wherein the biological indicator further comprises one or more excipients.

21. The sterilization indicator of claim 20 wherein the excipient comprises one or more carbohydrates.

22. The sterilization indicator of claim 20 wherein the excipient comprises trehalose.

23. The sterilization indicator of claim 20 wherein the excipient comprises sucrose, glucose, maltose, dextran, starch, agarose, cellulose, protein, phosphonate, buffering agent, wax, lipid, oil, or a mixture of two or more thereof.

24. The sterilization indicator of claim 1 wherein the biological indicator further comprises vancomycin resistant *enterococci, methicillin* resistant *Staphyloccus aureus, Mycobacterium cheloni*, or a mixture of two or more thereof.

25. The sterilization indicator of claim 1 wherein the biological indicator further comprises one or more prions.

26. The sterilization indicator of claim 1 wherein the carrier comprises paper, the biological indicator comprises spores of *Geobacillus stearothermophilus*, and the support comprises polystyrene.

27. The sterilization indicator of claim 1 wherein the time required to incubate the biological indicator is from about 0.1 to about 4 hours.

28. The sterilization indicator of claim 1 wherein the carrier has a surface area in the range from about 5 to about 50 mm$^2$ and the time required to incubate the biological indicator is from about 0.1 to about 4 hours.

29. A sterilization indicator, comprising:
  a carrier, the carrier having a first surface and a second surface, the first surface having an area in the range from about 1 to about 80 mm$^2$;
  a support, the support having a first section and a second section, the carrier overlying the first section of the support, the second surface of the carrier being adhered to the first section of the support; and
  a biological indicator supported by the first surface of the carrier, the biological indicator comprising bacterial spores, the first section of the support having a length and the second section of the support having a length, the ratio of the length of the second section of the support to the length of the first section of the support being in the range from about 2:1 to about 12:1, the second section of the support being of sufficient dimension to function as a handle to permit handling the sterilization indicator without contacting the biological indicator;
  the sterilization indicator being formed by applying the biological indicator to the carrier and then adhering the carrier to the support, the carrier being adhered to the support using sonic welding, the carrier having a surface area in the range from about 1 to about 80 mm$^2$, the volume of incubation medium needed to incubate the biological indicator being in the range from about 0.1 to about 5 ml, the time required to incubate the biological indicator being in the range from about 0.1 to about 48 hours,
  wherein the sonic welding, when applied to the carrier with the biological indicator applied, exhibits no significant difference in the biological indicator following the sonic welding as compared to prior to the sonic welding, and
  wherein the biological indicator comprises *Geobacillus stearothermophilus*.

30. The sterilization indicator of claim 29 wherein the time required to incubate the biological indicator is from about 0.1 to about 4 hours.

31. The sterilization indicator of claim 29 wherein the carrier has a surface area in the range from about 5 to about 50 mm$^2$.

32. The sterilization indicator of claim 29 wherein the carrier has a surface area in the range from about 5 to about 50 mm$^2$ and the time required to incubate the biological indicator is from about 0.1 to about 4 hours.

* * * * *